United States Patent [19]

Hartlaub et al.

[11] Patent Number: 4,943,295

[45] Date of Patent: Jul. 24, 1990

[54] SURGICAL CUTTING TOOL

[76] Inventors: Thaddeus J. Hartlaub, 6765 Schroeder Rd.; Mark T. Hartlaub, 14 Celia Ct., both of Madison, Wis. 53711; Paul P. Hartlaub, 1135 S. 23rd St., Milwaukee, Wis. 53204

[21] Appl. No.: 218,072

[22] Filed: Jul. 13, 1988

[51] Int. Cl.$^5$ .................. A61B 17/32; A61B 19/00
[52] U.S. Cl. ..................... 606/131; 606/167; 30/329; 30/346.5
[58] Field of Search ............... 128/304, 305, 355, 757; 604/22; 30/329, 334, 337, 314, 346.57, 346.58, 346.59, 346.60, 346.5; 606/131, 132, 167

[56] References Cited

U.S. PATENT DOCUMENTS

| | | | |
|---|---|---|---|
| 1,174,932 | 3/1916 | Grenier | 128/305 |
| 1,893,524 | 1/1933 | Shanley | 128/304 |
| 1,934,151 | 11/1933 | Slama et al. | 30/346.58 |
| 2,035,110 | 3/1936 | Becker et al. | 30/346.59 X |
| 2,041,778 | 5/1936 | Peters | 30/346.57 X |
| 3,583,403 | 6/1971 | Pohl . | |
| 3,688,407 | 9/1972 | Paquette . | |
| 3,961,418 | 6/1976 | Neveu . | |
| 4,038,986 | 8/1977 | Mahler . | |
| 4,221,222 | 9/1988 | Detsch . | |
| 4,438,767 | 3/1984 | Nelson . | |
| 4,651,734 | 3/1987 | Doss et al. . | |
| 4,690,139 | 9/1987 | Rosenberg . | |

Primary Examiner—Michael H. Thaler
Attorney, Agent, or Firm—Lathrop & Clark

[57] ABSTRACT

A surgical cutting tool which may be used in cutting away protruberances from the skin of an individual includes a thin flexible blade including two side margins and a front margin which is keen-edged, and two finger grips which each include an engagement surface affixed to and extending along one side margin of the blade, and an outwardly facing gripping surface so that the tool can be held by the finger grips and thereby safely, easily and comfortably bent into an arcuate shape for cutting, by bringing the finger grips closer together. Preferably each gripping surface forms a rounded notch conforming in approximate shape to a finger. The gripping surface forming the notch may include gripping protrusions which enable a user's fingers to grip the tool by the finger grips firmly. The tool preferably includes a sheath-like guard formed from flexible material which is affixed to and extends along and covers a rear margin of the blade between the finger grips. Although the guard protects a user of the tool from the keen-edged blade rear margin, the flexible material from which it is formed allows the user to bend the blade without substantial resistance from the guard.

13 Claims, 2 Drawing Sheets

SURGICAL CUTTING TOOL

Background of the Invention

1. Field of Invention

This invention pertains generally to the field of surgical cutting tools, and particularly to a surgical cutting tool which may be safely and easily bent into an arcuate shape to cut away protruberances on the skin of a patient.

2. Description of the Prior Art

Various types of surgical cutting tools have been utilized for cutting skin or for cutting away protruberances on the skin such as moles. Perhaps the most common such tool is the scalpel which is used much like a knife. However, scalpels may be difficult to use when cutting away protruberances on the skin such as moles because the blades are generally stiff. Therefore the individual using the scalpel has to cut at an incline to the skin surface all the way around the mole to remove the mole and any subsurface portion thereof.

As a result, many medical professionals have found it necessary to take a conventional, thin, flexible steel razor blade and to bend it into an arcuate or U-shape to cut away the mole. Typically, the individual using the blade grasps the sides of the blade, squeezes inwardly to bow the blade outwardly into an arcuate shape. The user then takes the U-shaped bent blade and places the bottom of the U against the mole and scrapes it away. Since the blade is bent into an arcuate shape, the lower portion of the blade arc can be used to cut the mole out below the surface of the skin, thereby assuring that the entire mole is actually removed. Since a conventional razor blade is quite thin, the sides of the blade are quite uncomfortable to the user's fingers, and might even cut the fingers. Also, the keen front and rear margins of these blades extend to the sides of the blade which the user grasps, and therefore present an additional danger to the fingers.

Summary of the Invention

The present invention is summarized in that a surgical cutting tool, which may be used in cutting away protruberances from the skin, includes a thin flexible blade including two side margins and a front margin which is keen-edged; and two finger grips which are each a body of material which includes an inwardly facing engagement surface affixed to and extending along one side margin of the blade, and an outwardly facing gripping surface spaced laterally outwardly from the side margin of the blade. Each gripping surface is substantially thicker than the blade so that the tool can be held by the gripping surfaces and the blade bent safely, easily and comfortably into an arcuate shape for cutting, by bringing the two finger grips closer together. Preferably each finger grip extends from the keen-edged blade front margin to the rear margin of the blade. Furthermore, the tool preferably includes a guard which is a sheath-like body formed of a flexible material which includes an engaging surface which is affixed to and extends along and covers a rear margin of the blade between the finger grips. Since the guard is formed from a flexible material, the guard does not inhibit the blade from being bent. Each gripping surface preferably forms a rounded notch conforming in approximate shape to the roundness of a finger. The gripping surface forming the notch may include gripping protrusions within the notch which enable a user's fingers to grasp the tool firmly by the finger grips.

A primary object of the invention is to provide a flexible surgical cutting tool which may be safely, easily and comfortably bent into a U-shape for cutting away skin protruberances.

A second object of the invention is to provide a surgical cutting tool which takes advantage of the flexibility of thin, resilient, steel razor blades, but which enables the user to handle such a blade safely without destroying its flexibility.

Another object of the invention is to provide a surgical cutting tool which may be formed in part from a double-edged, thin, flexible, steel razor blade on which one of the edges is covered by a flexible guard which protects the user from that edge, but at the same time allows the user to bend the steel blade into an arcuate shape.

Other objects, features, and advantages of the invention will be apparent from the following detailed description taken in conjunction with the accompanying drawings wherein a preferred embodiment of the invention has been selected for exemplification.

Description of the Preferred Embodiment

Figure 1:
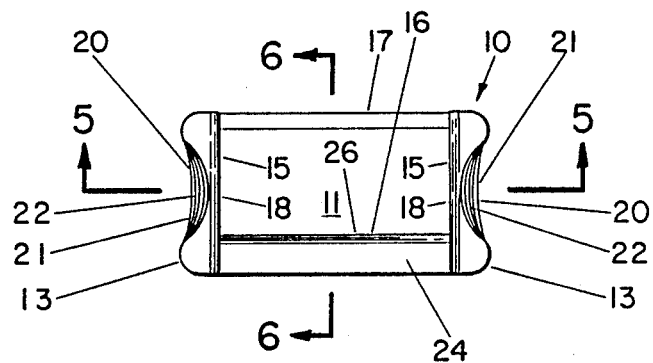
FIG. 1 is a top plan view of the surgical cutting tool.

Referring more particularly to the drawings, wherein like numbers refer to like parts, FIG. 1 shows a surgical cutting tool 10 which may be used in cutting away protruberances on the skin such as moles. As shown, the tool 10 includes a fairly conventional thin, flexible, resilient, rectangular steel razor blade 11 and two affixed finger grips 13 which facilitate holding and bending the blade 11 into an arcuate or U-shape for cutting as shown in FIG. 7.

Figure 5:
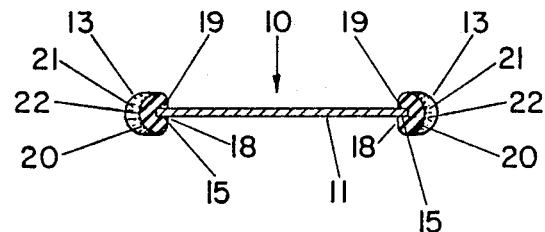
FIG. 5 is a sectional view taken along section line 5—5 of FIG. 1.
Figure 6:
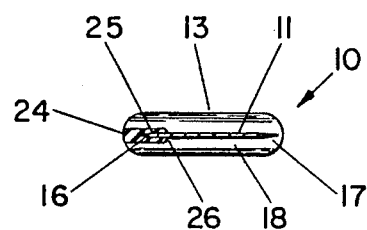
FIG. 6 is a sectional view taken along section line 6—6 of FIG. 1.

As shown in FIGS. 1, 3, 5, and 6, the blade includes two parallel side margins 15, a rear margin 16, and a front margin 17 which is keen-edged. Although the blade 11 may be a conventional blade, it is preferred that the blade 11 not have the holes which typically are centrally positioned on conventional blades for locking them in position within a razor. Each finger grip 13 is a body of material which includes an inwardly facing engagement surface 18 which is affixed to and which extends along one of the side margins 15 from the keen-edged blade front margin 17 to the rear margin 16 of the blade 11. As shown in FIG. 5, each finger grip 13 actually covers the entire corresponding blade side margin 15 to thereby protect the user who squeezes the blade 11 into an arcuate shape. Thus each engagement surface 18 actually forms a shallow slit 19 into which the affixed side margin 15 is ensheathed or covered. The finger grips 13 may be formed from plastic, rubber or any other material which can be formed. Materials having a relatively high coefficient of friction may be preferable, though, to prevent slippage while being held. The material forming the slit 19 is preferably bonded or otherwise firmly affixed to the blade side margin 15.

Figure 2:
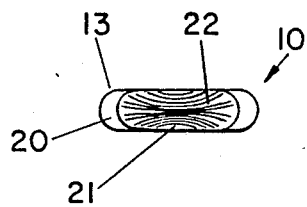
FIG. 2 is a side elevational view of the surgical cutting tool of FIG. 1.
Figure 3:
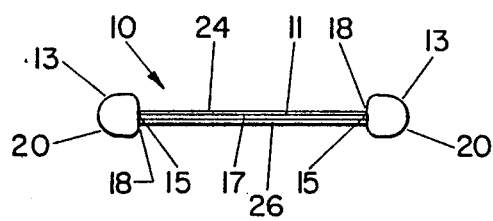
FIG. 3 is a front elevational view of the surgical cutting tool of FIG. 1.
Figure 4:
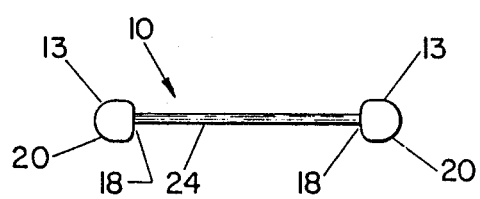
FIG. 4 is a rear elevational view of the surgical cutting tool of FIG. 1.

Each finger grip 13 further includes an outwardly facing gripping surface 20 which is spaced laterally outwardly from the adjacent blade side margin 15. Each gripping surface 20 is preferably fairly thick when compared to the blade 11 thickness so that the finger grips 13 present a relatively large area to a user's fingers, when compared to the side margin 15 of the blade 11. The gripping surfaces 20 each form a rounded notch 21 conforming in approximate shape to a finger as shown in FIGS. 1, 2 and 5. The gripping surface 20 forming the notch 21 includes ridge-like gripping protrusions 22 which extend substantially from a front to a rear of the notch 21. The ridged protrusions 22 are roughly parallel to the blade side margin 15, although they do curve slightly away from a centerline of the finger grip 13 as they extend to the front and rear of the notch 21.

Figure 7:
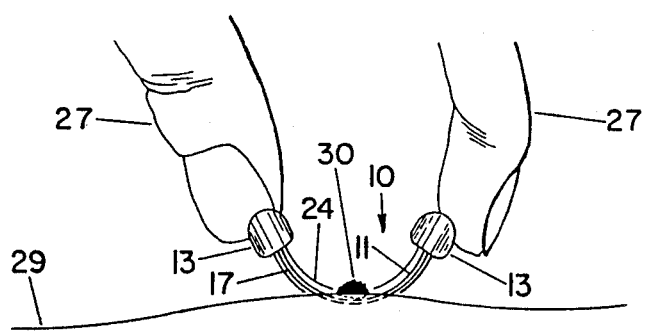
FIG. 7 is a front view of the surgical cutting tool of FIG. 1 being utilized to cut away a mole from the skin of a patient.

As shown in FIG. 7, a user's finger pressure on the finger grips 13 forces the finger grips 13 substantially close together which forms the keen-edged front margin 17 of the blade 11 into a variable convex U-shaped cutting edge. The lower portion of the U-shaped keen-edged front margin 17 extends forwardly of the ends of the user's fingers, and bottom or most extended portion of the U-shaped blade 11 extends below a limited area of the skin surface underlying a skin protuberance which is generally tangential to the keen-edged front margin 17 of the blade 11. The blade 11 undercuts small protuberances on the surface of the human skin, and will even remove a small amount of skin tissue which underlies the protuberance. It can be seen that the radius of the arc of the U-shaped blade 11 is inherently dependent upon the degree to which the fingers of the user reduce the distance between the finger grips as pressure is applied. The greater the applied finger pressure, the closer the finger grips 13 come to one another, increasing the tightness of the arc of the U-shaped keen-edged front margin 17 and thereby allowing a deeper cut into the skin for a given width of cut.

On page 6, line 8-10, delete "Alternatively, the tool 10 could be used for other purposes such as removing blemishes from fruits or vegetables."

As shown in FIGS. 1, 3, 4 and 6, a guard 24 which is a sheath-like body formed from a flexible material extends between the finger grips 13 along the rear margin 16 of the blade 11 to protect the user from that margin 16. The guard 24 includes an engaging surface 26 which is affixed to the blade 11. Since the guard 24 is formed from a flexible material such as plastic or rubber, the blade 11 can be bent by the user without substantial resistance from the guard 24. Preferably the sheath-like guard 24 covers the entire rear margin 16 between the finger grips 13. Thus the engaging surface 26 actually forms a slit 25 into which the entire rear margin 16 is ensheathed. The material forming the slit 25 within the guard 24 may be bonded or otherwise firmly affixed to the blade rear margin 16. In particular, the guard 24 should be affixed to the rear margin 16 or formed so that the keen-edged rear margin 16 does not cut or break through the guard 24. The guard 24 may be a separate structure affixed to the finger grips 13, or may be formed integrally with the finger grips 13 so as to form a unitary structure therewith. The finger grips 13 and guard 24 together form a preferred blade holder. In another alternative, the guard 24 might be removable so that it could be affixed to the blade front margin 17 and the rear margin 16 used for cutting.

Preferably the surgical cutting tool will be manufactured and packaged within sterile conditions. The surgical cutting tool 10 may be used to remove protuberances on the skin such as moles quickly, safely and effectively. Alternatively, the tool 10 could be used for other purposes such as removing blemishes from fruits or vegetables. As shown in FIG. 7, the gripping surfaces 20 of the tool 10 are grasped by the user's fingers 27, and then are squeezed toward each other so that the blade 11 bows downwardly into an arcuate shape. As shown in FIG. 7 in dashed lines, the blade 11 actually will cut below the surface 29 of the skin to thereby remove the entire mole 30. After the tool 10 is used once, it may be disposed of.

As shown in FIG. 7, the user's fingers 27 touch only the finger grips 13 and not any portion of the blade 11. The user is not required to touch either thin blade side margin 15 or the corners where the side margins 15 and keen-edged front margin 17 or rear margin 16 meet the side margins 15. With the addition of the guard 24, the unnecessary keen-edged rear margin 16 is essentially eliminated. Thus the present invention significantly decreases the chances that the blade might cut the user's fingers 27. The relatively larger area presented by the finger gives increased control over the tool 10 and grips 13 to the user's fingers also greatly decreases the chances that the tool 10 might snap out of the user's fingers, endangering both the user and the patient.

It is to be understood that the present invention is not limited to the particular arrangement and embodiments of parts disclosed and illustrated herein, nor to the materials specified, but embraces all such modified forms thereof as come within the scope of the following claims.

What is claimed is:

1. A surgical cutting tool for cutting below the surface of human skin, comprising:
   (a) a thin flexible blade which includes two side margins and a front margin which is keen-edged; and
   (b) two finger grips for gripping by the fingers of a user, each finger grip being a body of material which includes an inwardly facing engagement surface affixed to and extending along one side margin of the blade; and an outwardly facing gripping surface spaced laterally outwardly from the side margin of the blade, the gripping surface presenting a relatively large surface area compared to the side margin of the blade so that the tool can be controlled and held safely by finger engagement of the gripping surfaces and having a rounded notch which conforms in approximate shape to a finger;
   (c) the flexible blade being readily bendable in response to finger pressure applied to the relatively large surface areas of the gripping surfaces of the two finger grips so that the keen-edged front margin of the flexible blade presents a variable convex U-shaped cutting edge for cutting a selected depth beneath a limited area of skin surfaces.

2. The tool of claim 1 wherein each gripping surface forming the notch includes gripping protrusions within the notch which enable a user's fingers to grip the tool firmly by the finger grips.

3. The tool of claim 2 wherein the protrusions are ridge-like and extend substantially from a front to a rear of the notch.

4. A surgical cutting tool, comprising:
(a) a thin flexible blade which includes two side margins and a front margin which is keen-edged;
(b) two finger grips, each finger grip being a body of material which includes an inwardly facing engagement surface affixed to and extending along one side margin of the blade; and an outwardly facing gripping surface spaced laterally outwardly from the side margin of the blade, the gripping surface being substantially thicker than the blade so that the tool can be held safely by the gripping surfaces and the keen-edged front margin of the blade bent into a U-shape by bringing the finger grips substantially closer together; and
(c) a guard having a sheath-like body formed of a flexible material which includes an engaging surface which is affixed to and which extends along and covers a rear margin of the blade between the finger grips, the flexible material allowing the blade to bend.

5. The tool of claim 4 wherein the engaging surface forms a slit into which the rear margin is ensheathed.

6. The tool of claim 5 wherein the material forming the slit within the guard is bonded to the blade rear margin.

7. The tool of claim 4 wherein the guard and finger grips are integrally formed as a unitary structure.

8. A blade holder for safely forming a thin flexible blade with two side margins and a keen-edged front margin into a surgical cutting tool for removing portions of human skin by cutting below the surface of the skin, comprising: two finger grips for gripping by the fingers of a user, each finger grip being a body of material which includes an inwardly facing engagement surface which can be affixed to and extend along one blade side margin, and an outwardly facing gripping surface which is spaced laterally outwardly from the blade side margin when the finger grips are affixed to the blade, the gripping surface presenting a relatively large area for gripping compared to the area of the side margin of the blade so that the blade holder and blade can be controlled and held safely by finger engagement of the gripping surfaces so that the flexible blade may be readily bent in response to finger pressure applied to the relatively large surface areas of the gripping surfaces of the two finger grips and the keen-edged front margin of the flexible blade presents a variable convex U-shaped cutting edge for cutting a selected depth beneath a limited area of skin surface and wherein each gripping surface has a rounded notch which conforms in approximate shape to a finger.

9. The blade holder of claim 8 wherein each gripping surface forming the notch includes gripping protrusions within the notch which enable a user's finger to grip the blade holder and blade firmly by the finger grips.

10. The blade holder of claim 9 wherein the protrusions are ridge-like and extend substantially from a front to a rear of the notch.

11. A blade holder for safely handling a thin flexible blade with two side margins and a keen-edged front margin, comprising:
(a) two finger grips being a body of material which includes an inwardly facing engagement surface which can be affixed to and extend along one blade side margin, and an outwardly facing gripping surface which is spaced laterally outwardly from the blade side margin when the finger grips are affixed to the blade, the gripping surface being substantially thicker than the blade so that the blade holder and blade can be held safely by the gripping surfaces and the keen-edged front margin of the blade bent into a U-shape by bringing the finger grips substantially closer together; and
(b) a guard having a sheath-like body formed of a flexible material which includes an engaging surface which is to be affixed to a rear margin of the blade so that the guard extends along and covers the rear margin between the finger grips, the flexible material allowing the blade to bend.

12. The blade holder of claim 11 wherein the engaging surface forms a slit into which the blade rear margin an be ensheathed.

13. The blade holder of claim 11, wherein the guard and finger grips are integrally formed as a unitary structure.

* * * * *

UNITED STATES PATENT AND TRADEMARK OFFICE
CERTIFICATE OF CORRECTION

PATENT NO. : 4,943,295

DATED : July 24, 1990

INVENTOR(S) : Hartlaub, et al.

It is certified that error appears in the above-identified patent and that said Letters Patent is hereby corrected as shown below:

Column 3, line 24, "close" should be -- closer --.

Column 3, line 28, "and bottom" should be -- and the bottom --.

Column 3, lines 44-46, cancel the entire sentence beginning with "On page 6," to and including "or vegetables."".

Column 4, lines 8-10, delete "Alternatively, the tool 10 could be used for other purposes such as removing blemishes from fruits or vegetables."

Column 4, line 28, delete "gives increased control over the tool 10 and" after the word "finger".

Column 4, line 29, insert -- gives increased control over the tool 10 and -- after the word "fingers".

Column 6, line 19, insert -- , each finger grip -- after the word "grips".

Column 6, line 39, "an" should be -- can --.

UNITED STATES PATENT AND TRADEMARK OFFICE
CERTIFICATE OF CORRECTION

PATENT NO. : 4,943,295

DATED : July 24, 1990

INVENTOR(S) : Hartlaub, et al.

It is certified that error appears in the above-identified patent and that said Letters Patent is hereby corrected as shown below:

Column 6, line 19, insert -- , each finger grip -- after the word "grips".

Column 6, line 39, "an" should be -- can --.

Signed and Sealed this

Fourth Day of August, 1992

Attest:

DOUGLAS B. COMER

*Attesting Officer*  *Acting Commissioner of Patents and Trademarks*